US005424475A

United States Patent [19]

Boggs et al.

[11] Patent Number: 5,424,475

[45] Date of Patent: * Jun. 13, 1995

[54] THERMAL IMAGING DYE PRECURSORS

[75] Inventors: Roger A. Boggs, Wayland, Mass.; Alan L. Borror, Cape Elizabeth, Me.; Patrick R. Conlon, Wakefield, Mass.; Richard L. Cournoyer, San Jose, Calif.; Ernest W. Ellis, Leverett; David P. Waller, Lexington, both of Mass.

[73] Assignee: Polaroid Corporation, Cambridge, Mass.

[ * ] Notice: The portion of the term of this patent subsequent to Aug. 17, 2010 has been disclaimed.

[21] Appl. No.: 729,426

[22] Filed: Jul. 12, 1991

Related U.S. Application Data

[63] Continuation-in-part of Ser. No. 277,014, Nov. 28, 1988, abandoned, which is a continuation-in-part of Ser. No. 221,032, Jul. 18, 1988, abandoned.

[51] Int. Cl.$^6$ .................... C07C 271/14; C07C 271/28

[52] U.S. Cl. ...................................... 560/27; 548/209; 548/366.7; 548/368.4; 558/50; 558/272; 564/168

[58] Field of Search .......................... 560/27; 564/168; 548/209, 366.7, 368.4; 558/50, 272

[56] References Cited

U.S. PATENT DOCUMENTS

| | | | |
|---|---|---|---|
| 3,409,457 | 11/1968 | Menzel | 117/36.8 |
| 4,602,263 | 7/1986 | Borror et al. | 346/201 |
| 4,720,449 | 7/1988 | Borror et al. | 430/338 |

FOREIGN PATENT DOCUMENTS

| | | | |
|---|---|---|---|
| 57-46239 | 3/1982 | Japan . | |
| 1176590 | 12/1987 | Japan | 564/168 |

OTHER PUBLICATIONS

James, T. H., The Theory of the Photographic Process, Fourth Edition, MacMillan Publishing Co., Inc., New York, May 1977, pp. 353–362.

T. W. Greene, Protective Groups in Organic Synthesis, John Wiley & Sons July (1981), p. vii. (Preface).

*Primary Examiner*—José G. Dees
*Assistant Examiner*—B. Frazier
*Attorney, Agent, or Firm*—Carol A. Loeschorn; Edward W. Black

[57] ABSTRACT

Colorless precursors of preformed image dyes are provided which are useful as the color image-forming materials in thermal imaging systems. These colorless precursors possess at least one thermal protecting group that undergoes fragmentation upon heating and at least one leaving group that undergoes irreversible elimination upon heating, said protecting and leaving groups maintaining the precursor in its colorless form until heat is applied to effect removal of these groups whereby the precursor is converted to an image dye.

14 Claims, No Drawings

THERMAL IMAGING DYE PRECURSORS

CROSS REFERENCE TO RELATED APPLICATION

This application is a continuation-in-part of application Ser. No. 277,014, filed Nov. 28, 1988, now abandoned, which application is a continuation-in-part of application Ser. No. 221,032 filed Jul. 18, 1988, now abandoned.

BACKGROUND OF THE INVENTION

This invention relates to heat-sensitive recording elements particularly useful for making color hard copy, to a method of imaging employing said elements and to novel colorless precursors of preformed image dyes useful as the color image-forming materials.

Dye precursor molecules have been suggested previously which become irreversibly colored by the loss of a single group. For example, Japanese Patent Kokai No. 57-46239, Laid Open Mar. 16, 1982, discloses indoaniline dye precursors which possess an alkyl/aryl sulfonyl group that irreversibly cleaves from the precursor molecule upon exposure to light, usually ultraviolet light, with the result that the precursor is converted to its colored form and cannot revert back to its leuco or colorless form. U.S. Pat. No. 3,409,457 to Karl-Heinz Menzel discloses colorless dye precursors which possess an acylamino group that cleaves from the precursor molecule upon heating to yield a colored azomethine dye. The conversion of these leuco compounds into the azomethine dyes is accelerated by using alkalis such as alkali alcoholates. The acylamino and alkyl/aryl sulfonyl groups employed in the colorless dye precursors of these references depart from the precursor molecule to effect conjugation and form a dye chromophore.

U.S. Pat. No. 4,602,263 to Alan L. Borror, Ernest W. Ellis and Donald A. McGowan discloses the stabilization of a Colorless dye precursor by employing a tertiary-alkoxycarbonyl group, for example, t-butoxycarbonyl, as a thermally removable protecting group. This protecting group is removed by unimolecular fragmentation upon heating, which fragmentation reaction is irreversible. U.S. Pat. No. 4,720,449 to Alan L. Borror and Ernest W. Ellis discloses colorless di- and triarylmethane compounds possessing a masked acylation substituent which undergoes irreversible fragmentation upon heating to liberate the acyl group for effecting an intramolecular acylation reaction whereby the compounds are rendered colored.

SUMMARY OF THE INVENTION

According to the present invention, it has been found that the use of both a thermally removable protecting group and a leaving group, i.e., a group that effects conjugation upon splitting off from the leuco molecule, are required to stabilize the colorless form of a preformed dye precursor molecule. In particular, it has been found that both a leaving group (LG) and a stabilizing thermally removable protecting group (TPG) can be incorporated into a preformed dye molecule to provide a colorless dye precursor that is stable at ambient temperatures but capable of being irreversibly converted to the dye chromophore upon heating. This conversion from the colorless to colored form is achieved by the removal of one or more thermal protecting groups and the irreversible elimination of one or more leaving groups, thereby effecting conjugation in the chromophore portion and color formation.

It is, therefore, among the objects of the present invention to provide certain colorless dye precursor compounds useful in thermal imaging, to provide heat-sensitive recording elements employing these compounds and to provide a method of producing color images employing said elements.

DETAILED DESCRIPTION OF THE INVENTION

In particular, the compounds of the present invention comprise a colorless precursor of a preformed image dye substituted with (a) at least one thermally removable protecting group that undergoes fragmentation from said precursor upon heating and (b) at least one leaving group that is irreversibly eliminated from said precursor upon heating, said thermal protecting and leaving groups maintaining said precursor in its colorless form until heat is applied to effect removal of said protecting and leaving groups whereby said colorless precursor is converted to an image dye.

As described by Nassau, Kurt in The Physics and Chemistry of Color, John Wiley and Sons, New York, 1983, p. 110, a dye is defined as a "color-producing chromogen which is composed of a basic chromophore ("colorbearing") group, not necessarily producing color, to which can be attached a variety of subsidiary groups, named auxochromes ("color increasers"), which lead to the production of color. Chromophores include carbon-carbon double bonds, particularly in conjugated systems containing alternating single and double bonds as in the carbon chain Structure (6-1), as well as in the azo

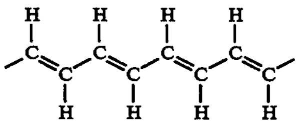

(6-1)

—N=N— (6-2)

 (6-3)

—N=O (6-4)

group, Structure (6-2), thio group, Structure (6-3), and nitroso group, Structure (6-4), among others. Auxochromes include groups such as $—NH_2$, $—NR_2$ where R represents an organic group, $—NO_2$, $—CH_3$, —OH, —OR, —Br, —Cl, and so on. We now recognize that some of these auxochromes are electron donors, such as $—NH_2$, and some are electron acceptors, such as $—NO_2$ or —Br." For a further discussion of the auxochromophoric system of dyes, see Gilman, Henry, Organic Chemistry, An Advanced Treatise, Vol. III, John Wiley & Sons, New York, 1953, pp. 247–55; and Venkataraman, K., The Chemistry of Synthetic Dyes, Vol. I, Academic Press, Inc., New York, 1952, pp. 323–400.

In accordance with the present invention, the thermally removable protecting group(s) and leaving group(s) are substituted on a preformed image dye so as to interrupt the conjugation of its colored auxochromophoric system and render it substantially colorless. The thermally removable protecting group(s) and leaving group(s) are used to stabilize the electron balance of the color-shifted structure such that the colorless form is maintained until application of heat causes removal of the protecting group(s) and loss of the leaving group(s). To avoid premature coloration under normal storage and handling conditions, the protecting group(s) selected should be capable of being removed from the colorless precursor molecule only at an elevated temperature. Usually, the thermally removable protecting group(s) are selected to provide a colorless dye precursor molecule that can be activated at a temperature above 100° C. The leaving group(s) and protecting group(s) are selected such that they will cleave from the precursor molecule at the desired rate upon application of heat.

As is well known in the art, color developers such as p-phenylenediamines are oxidized and react with couplers to form dyes of a wide variety of colors. Leuco dyes are intermediate in the formation of dyes. The couplers are classified as either 4-electron or 2-electron couplers depending on whether or not the leuco dye is in the same oxidation state as the resulting dye. Couplers which have a leaving group in the coupling site are 2-electron couplers. The leuco dyes derived from the 2-electron couplers go readily to the dye via elimination of the leaving group. No oxidation of the leuco dye is required for the transformation to dye, as illustrated below.

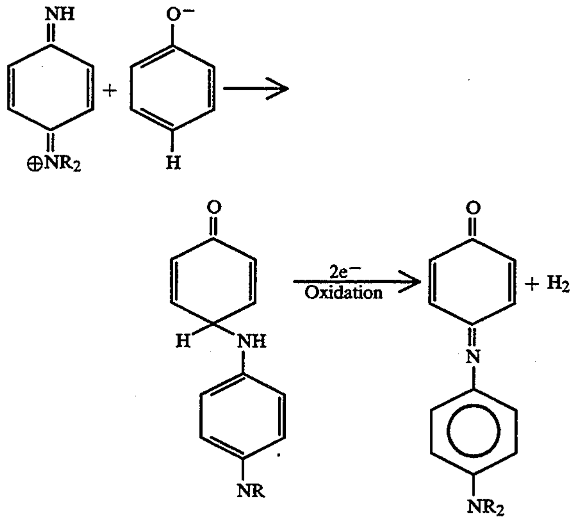

Leuco Dye Dye

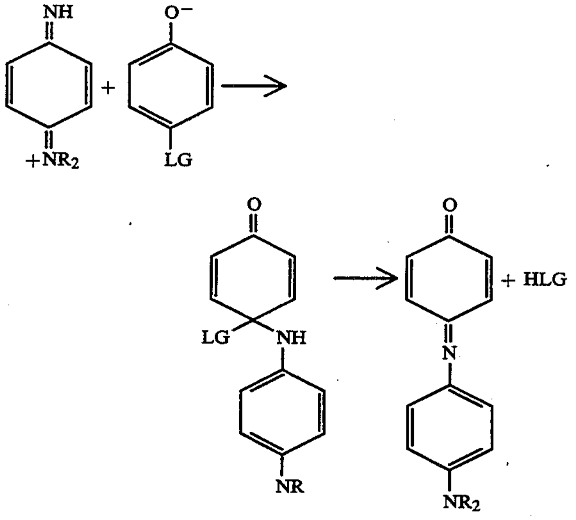

Leuco Dye Dye

The principle of this invention of employing both a stabilizing protecting group and a leaving group to design a heat activatable color-shifted dye precursor molecule may be applied to any of the various classes of dyes possessing, for example, an azo, imine or methine linkage such as azo, azine, azomethine, methine, di- and triarylmethane, indoaniline, indophenol and indamine dyes. One of the substituent groups, that is, one of said thermally removable protecting group and said leaving group may be bonded to an atom of the colorless chromophore portion of the precursor molecule and the other to an auxochrome, or both the protecting group and leaving group can be bonded to different atoms of the colorless chromophore portion of the molecule.

Illustrative dye precursor compounds of the present invention as derivatized with a thermally removable protecting group (TPG) and a leaving group (LG) are set forth below wherein A denotes an auxochromic group and Ar denotes an aryl group, such as a phenyl or naphthyl group, substituted or unsubstituted. Also shown is the dye obtained upon heating which results from the loss of the TPG and LG groups, which groups subsequent to cleavage and departure from the precursor molecule may undergo further fragmentation.

(a)

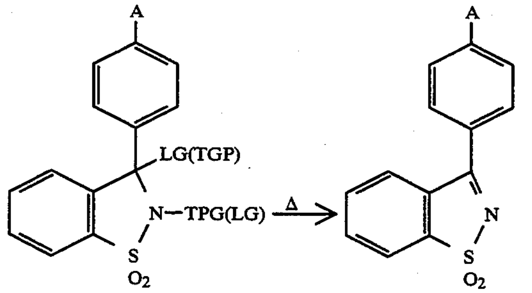

(b)

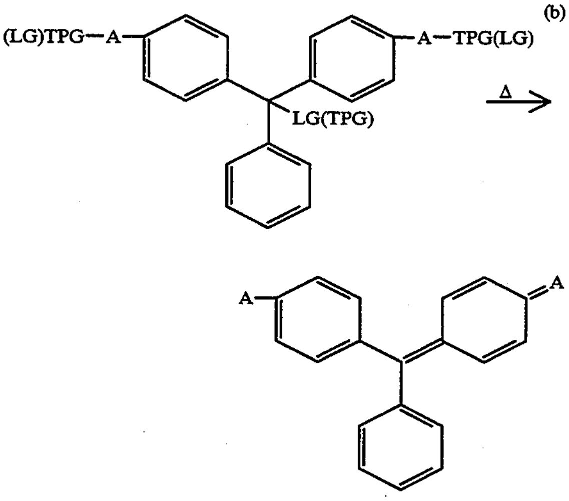

(c)

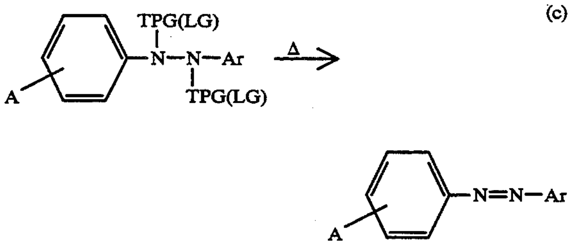

-continued
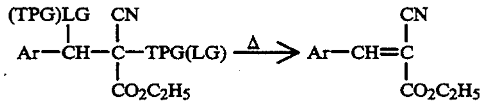
(d)
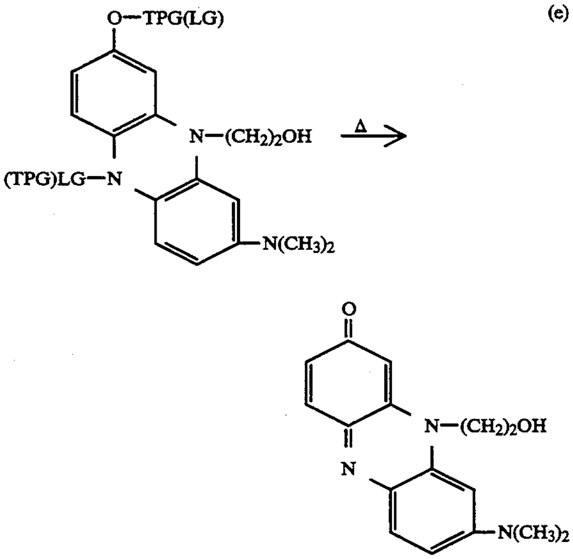
(e)
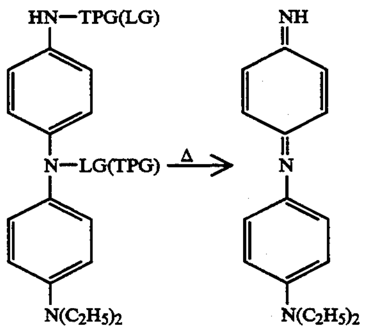
(f)
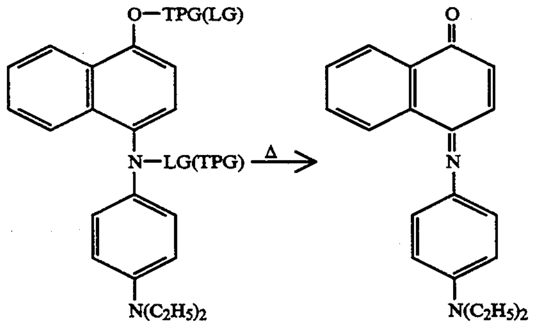
(g)
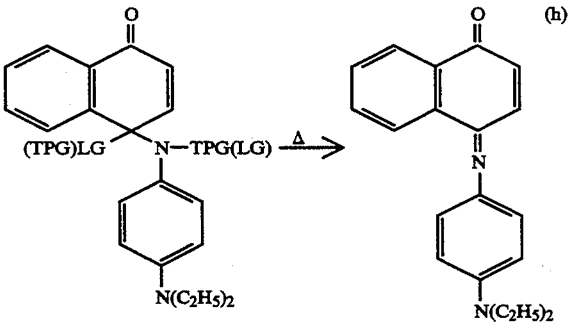
(h)
-continued
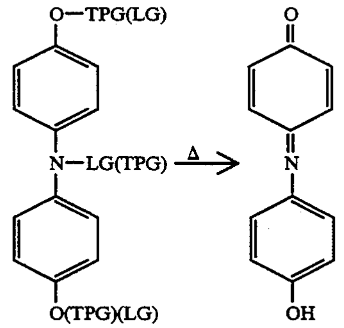
(i)
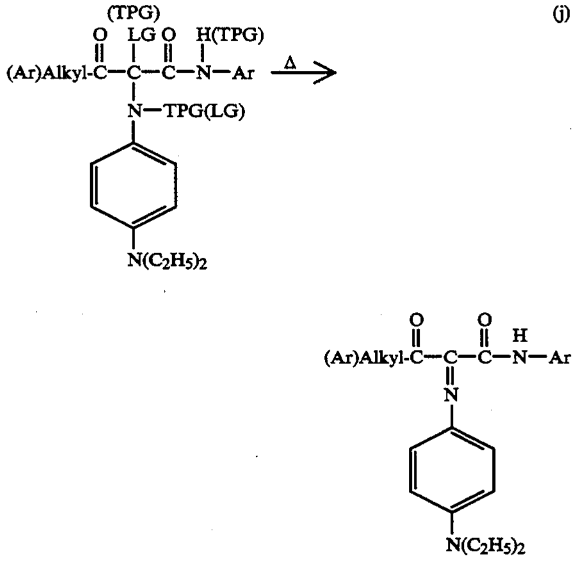
(j)
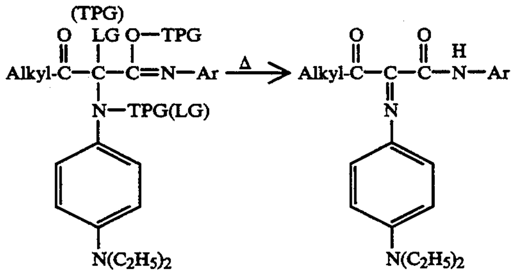
(k)
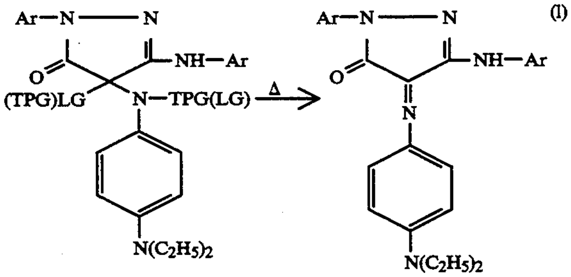
(l)
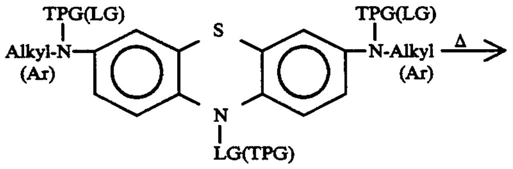
(m)

-continued

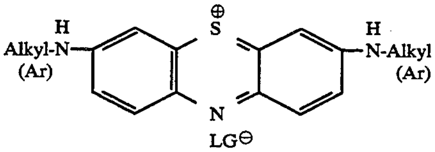

(n)

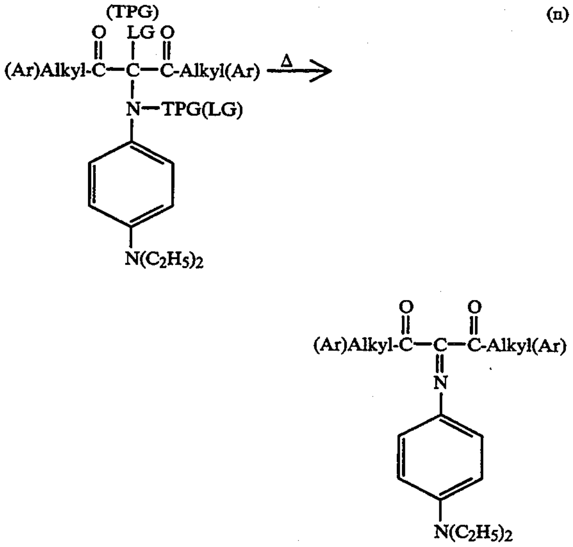

(o)

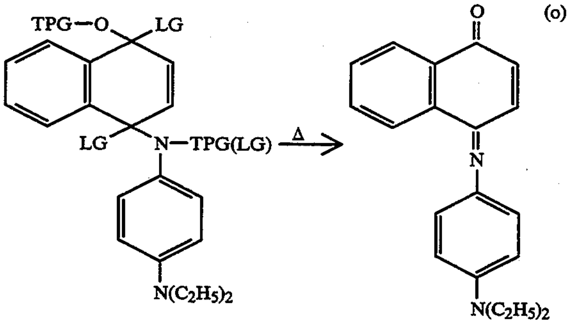

Examples of thermally removable protecting groups that can be used in the present invention include the following wherein EW denotes an electron-withdrawing group, i.e., a group having a positive sigma value as defined by Hammett's Equation.

(1)

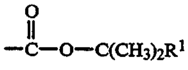

wherein $R^1$ is alkyl usually containing 1 to 6 carbon atoms or halomethyl, e.g., methyl substituted with one, two or three halo groups such as chloro or bromo or aryl usually phenyl, substituted or unsubstituted (2)

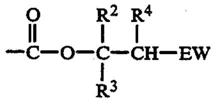

wherein $R^2$ and $R^3$ each are hydrogen, alkyl or aryl usually phenyl, $R^4$ is hydrogen, alkyl, aryl usually phenyl or EW and EW represents an electron-withdrawing group (3)

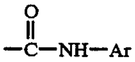

wherein Ar is aryl usually phenyl, substituted or unsubstituted (4)

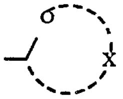

wherein X represents the atoms to complete, e.g., 2-tetrahydropyranyl, and (5)

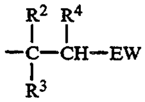

wherein $R^2$, $R^3$, $R^4$ and EW have the same meaning given above.

Illustrative electron-withdrawing groups include nitro, cyano, thiocyano, methylsulfonyl, phenylsulfonyl, tosyl, acetyl, formyl, benzoyl, carbomethoxy, carbethoxy, carbamyl, carboxy, N,N-(dibenzyl)sulfamoyl and trifluoromethylsulfonyl. These and other suitable electron-withdrawing groups are found in Lange's Handbook of Chemistry, Twelfth Edition, McGraw-Hill, Inc., 1979, Section 3, pages 3-134 to 3-137 and in A. J. Gordon and R. A. Ford, The Chemist's Companion, A Handbook of Practical Data, Techniques, and References, John Wiley & Sons, New York, 1972, pp. 144-155.

The thermally removable protecting groups of types (1) and (2) are used for substitution on nitrogen and the protecting groups of types (1) to (5) are used for substitution on oxygen, sulfur and active methylenes.

Leaving groups are well known and various such groups have been discussed by Charles J. M. Stirling, Acc. Chem. Res. 12, 198 (1979) and by Charles J. M. Stirling, et al., J. Chem. Soc. Chem. Commun., 941 (1975). Examples of leaving groups that can be employed in the present invention include heterocycles such as imidazolyl or

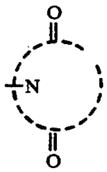

or

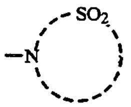

halo; hydroxy; SOR; SOAr; —SR; —$SO_2R$; —SAr; —$SO_2Ar$; —SeAr; —OAr; —OR; $P(O)(OR)_2$; —$C(R)_2EW$; —$C(R)(EW)_2$; —$CH(EW)_2$; —N(R)Ar; —N(Ar)Ar; —$N(Ar)CO_2CH_2Ar$; and —$N(R)CO_2Ar$ wherein EW represents an electron-withdrawing group, R is alkyl and Ar is aryl usually phenyl, unsubstituted or substituted with one or more substituents, for example, alkyl, alkoxy, halo, carboxy, nitro, cyano, —$SO_2$alkyl, —$SO_2$phenyl, tosyl and N,N-(dialkyl)amino wherein said alkyl usually contain 1 to 6 carbon atoms, Preferred leaving groups for substitution on nitrogen, oxygen and sulfur are alkyl and aryl sulfonyl groups, such as, —$SO_2Me$ and —$SO_2Ph$. Preferred leaving groups for substitution on carbon are phenoxy, unsubstituted or substituted with one or more groups, for example, alkyl usually having 1 to 20 carbon atoms, alkoxy usually having 1 to 20 carbon atoms, and carboalkoxy usually having 1 to 20 carbon atoms.

It will be apparent to one skilled in the art from the disclosure and examples herein that neither the protecting group nor the leaving group may be hydrogen.

The dye precursor compounds used in the present invention can be monomeric or polymeric compounds. Suitable polymeric compounds are those which, for example, comprise a polymeric backbone chain having dye precursor moieties attached directly thereto or through pendant linking groups. Polymeric compounds of the invention can be provided by attachment of the dye precursor moiety to the polymeric chain via carbon chains that do not affect color formation. For example, a monomeric dye precursor compound having an insulated reactable substituent group, such as an hydroxyl or amino group, can be conveniently reacted with a mono-ethylenically unsaturated and polymerizable compound having a functional and derivatizable moiety, to provide a polymerizable monomer having a pendant dye precursor moiety. Suitable mono-ethylenically unsaturated compounds for this purpose include acrylyl chloride, methacrylyl chloride, methacrylic anhydride, 2-isocyanatoethyl methacrylate and 2-hydroxyethyl acrylate, which can be reacted with an appropriately substituted dye precursor compound for production of a polymerizable monomer which in turn can be polymerized in known manner to provide a polymer having the dye precursor compound pendant from the backbone chain thereof.

In a preferred embodiment, the colorless dye precursors of the present invention comprise the coupling products of a p-phenylenediamine color developer and a dye-forming coupler which are substituted with a thermally removable protecting group(s) and a leaving group in the manner discussed above. These colorless precursor compounds have the structural formula:

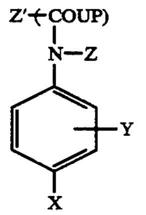

wherein:

COUP represents a dye-forming coupler moiety substituted in its coupling position with the remainder of the structure;

X is —NR'R" wherein R' and R" each are selected from hydrogen and lower alkyl containing 1 to 6 carbon atoms;

Y is hydrogen, alkyl, or substituted alkyl, e.g., hydroxymethyl or hydroxyethyl; and Z and Z' each are selected from a thermally removable protecting group and a leaving group provided one of Z and Z' is said protecting group and the other is said leaving group.

In these preferred precursor compounds, Z and Z' may be selected from the thermally removable protecting groups and the leaving groups enumerated above. The X substituent preferably is N,N-(dialkyl)amino wherein the alkyl groups are lower alkyl having 1 to 6 carbon atoms, particularly ethyl. Where Y is an alkyl substituent it also is usually lower alkyl having 1 to 6 carbon atoms, and preferably y is methyl and is positioned ortho to >N-Z The dye-forming coupler moiety may be any of the coupler moieties known or used in the photographic art to form a colored reaction product with oxidized color developers. Examples of coupler moieties that may be used for yellow dye-forming compounds are those derived from acylacetanilides such as benzoylacetanilides and particularly pivaloylacetanilides and variations of pivaloylacetanilides. Coupler moieties that may be used for magenta dye-forming compounds are those derived from pyrazolotriazoles, indazolones, pyrazolobenzimidazoles, and particularly, pyrazolones such as 1-aryl-5-pyrazolones. Coupler moieties that may be used for cyan dye-forming compounds are those derived from substituted phenols or substituted naphthols, particularly 2-carbonamido-phenols and 1-hydroxy-2-naphthamides. The formation of image dyes by the reaction between a color-forming coupler and the oxidation product of a color developer in color photographic processes is well known, and a review of these color-forming reactions and of color couplers including polymeric color couplers and color developers useful therein is found in T. H. James, The Theory of the Photographic Process, Fourth Edition, Macmillan Publishing Co., Inc., New York, 1977, pp. 335–362.

The colorless dye precursor compounds of the present invention may be synthesized using conventional techniques. For example, the colorless precursors of the di- and triarylmethane dyes may be prepared from appropriately substituted benzenes, e.g., anilines or phenols using condensation reactions employing aluminum chloride or zinc chloride or by employing Grignard or organolithium reactions. The thermal protecting and/or leaving groups may be incorporated into the starting materials and/or introduced subsequently. The colorless precursors of the azo dyes may be prepared by substituting a leaving group and a thermal protecting group on a hydrazobenzene compound. The colorless precursors of the methine dyes may be prepared by Michael addition of a nucleophile and capture of the subsequent intermediate anion with a thermal protecting group. The colorless precursors of the azine dyes may be prepared by reduction of azine dyes followed by substitution with the thermal protecting and leaving groups. The colorless precursors of the azomethine, indoaniline, indophenol and indamine dyes can be synthesized by the oxidative coupling of a color developer, for example, a p-phenylenediamine substituted with a thermal protecting or leaving group and a color-forming coupler substituted with a thermal protecting or leaving group as follows:

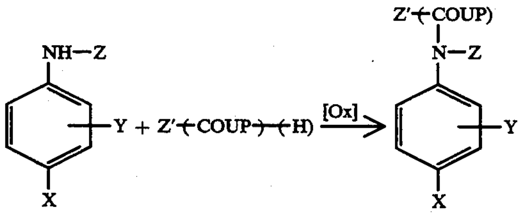

wherein X, Y, Z and Z′ have the same meaning given above. Also, the thermal protecting group and/or leaving group can be introduced subsequent to coupling.

Illustrative color-forming couplers that may be employed in the above reaction include:

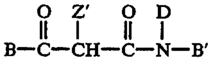 and 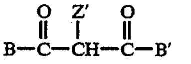 (i)

wherein B is selected from $(CH_3)_3C$—, $CH_3OCH_2(CH_3)_2C$—, $C_6H_5O(CH_3)_2C$— and phenyl, unsubstituted or substituted with one or more groups selected from alkyl, alkoxy, nitro, halo such as chloro, and carbonamido; B′ is phenyl, unsubstituted or substituted with one or more groups selected from alkyl, alkoxy, nitro, halo such as chloro and carbonamido, said phenyl group B′ being the same or different from said phenyl group B; D is hydrogen, alkyl usually lower alkyl containing 1 to 6 carbon atoms or acyl, e.g. acetyl; and Z′ has the same meaning given above.

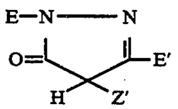 (ii)

wherein E is selected from benzimidazolyl and phenyl, unsubstituted or substituted with one or more groups selected from alkyl, alkoxy, amino, amino substituted with phenyl or substituted with one or two alkyl groups and halo such as chloro; E′ is selected from alkyl, aryl usually phenyl, amino, amino substituted with phenyl or substituted with one or two alkyl groups, heterocyclic amino, carbonamido, sulfonamido, guanidino and ureido; and Z′ has the same meaning given above.

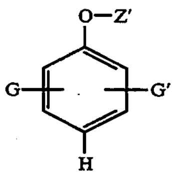 and 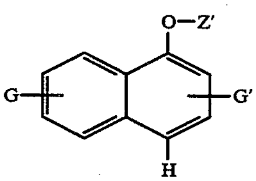 (iii)

wherein G is selected from hydrogen, alkyl, alkoxy, halo such as chloro and carbonamido; G′ is selected from hydrogen, carbonamido, perfluoroacylamido, ureido and carbamyl; and Z′ has the same meaning given above. In the phenol derivatives, G′ is usually 2-carbonamido (—$NHCOR_2$) and in the naphthol derivative, G′ is usually 2-carbamyl (—$CONR_2R_3$) wherein $R_1$ typically is alkyl, alkyl substituted with phenoxy, phenyl or phenyl substituted with phenoxy and $R_2$ and $R_3$, the same or different, typically are selected from hydrogen, alkyl, phenyl; p-alkoxyphenyl, p-chlorophenyl, p-nitrophenyl and p-sulfamylphenyl.

The following examples are given to further illustrate the present invention and are not intended to limit the scope thereof.

EXAMPLE 1

Preparation of the compound having the formula

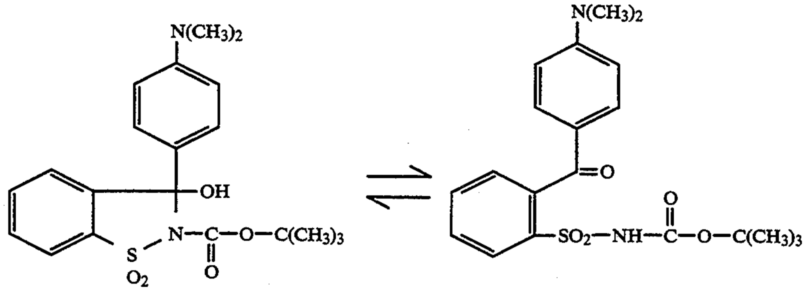

colorless "yellowish"

I. p-Bromo-N, N-dimethylaniline (12 g, 0.06 mole) in 150 ml of dry tetrahydrofuran was cooled in a dry ice bath and treated with 2.5M n-butyllithium (24 ml, 0.06 mole ) over 15 minutes.

II. Saccharin (11.2 g, 0.061 mole) in 100 ml dry tetrahydrofuran was cooled in a dry ice bath and treated with 2.5M n-butyllithium (24 ml, 0.06 mole) over 15 minutes.

The lithium saccharide solution (II) was added to the lithium dimethylanilide slurry (I) over 30 minutes at dry ice bath temperature, under nitrogen. The resulting solution was allowed to come to +5° C. over 35 minutes, recooled in a dry ice bath and treated with di-tert-butyl dicarbonate (29.5 g, 0.1.35 mole) in 40 ml tetrahydrofuran. The light orange solution was allowed to come to room temperature and kept overnight. Solids deposited were collected by filtration, triturated with ml water and refiltered. The water filtrate (pH 8) was saturated with carbon dioxide and extracted with methylene chloride. After drying over sodium sulfate, the solvent was removed under reduced pressure providing 2.5 g of amorphous, yellow solid; pmr, $C^{13}$ and IR spectra confirmed structure; m/e found: 404 (theory, 404). This material can be coated in its colorless form by appropriate selection of matrix.

EXAMPLE 2

Preparation of the Compound having the formula

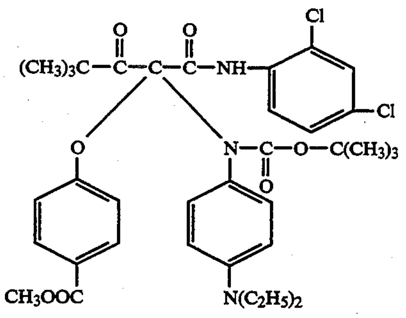

(a) 22.9 g (0.105 mole) of di-tert-butyl dicarbonate was added all at once to a mixture of 20.1 g (0.1 mole) of N,N-diethyl-p-phenylenediamine hydrochloride and 48 g (0.57 mole) of sodium bicarbonate in 250 ml methylene chloride. The mixture was allowed to stir overnight under an atmosphere of argon. The solids were filtered and washed with methylene chloride. The solvent was evaporated under reduced pressure to afford a dark oil. TLC on silica gel (methylene chloride:methanol 100:1) indicated a single product. The oil was triturated with hexanes and the glass vessel scratched to afford crystalline material. The bulk of material was treated with 150 ml hexanes, heated to reflux, filtered to remove insoluble impurities and cooled to crystallize the product having the formula

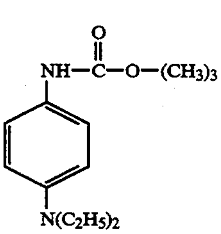

which was recovered in 83% by weight yield (22.9 g).

(b) Hydrogen chloride gas was bubbled into a suspension of 12.0 g (28.3 mmole) of the carboxylic acid compound having the formula

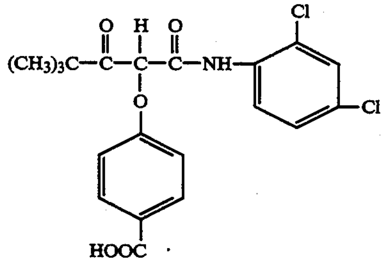

in 175 ml absolute methanol for about 30 minutes. Most of the carboxylic acid had dissolved after this time. The mixture was then heated at reflux for 2 hours during which time the remainder of the acid had dissolved. On cooling to room temperature the reaction product had begun to crystallize from the reaction solution. The mixture was cooled further in an ice bath and the crystalline product removed by filtration, washed with methanol and dried to afford 8.4 g (68% yield by weight) of the corresponding methyl ester. m/e 438

(c) A solution of 438.3 mg (1.0 mmole) of the methyl ester compound of step (b) and 264.4 mg (1.0 mmole) of the compound prepared in step (a) and 0.28 ml (202.4 mg, 2.0 mmole) of triethylamine in 10 ml methylene chloride was cooled to −78° C. Then 443.4 mg (1.0 mmole) of lead tetraacetate was added all at once to the above solution. The mixture was allowed to stir at −78° C. under an atmosphere of argon. An aliquot after 30 minutes showed almost no starting methyl ester compound as determined by TLC. The reaction product was chromatographed on a gravity column (25 mm×200 mm). The silica gel column was eluted with 500 ml methylene chloride:hexane (1:1) followed by methylene chloride:hexane (3:1). 40×9 ml fractions were collected and all fractions showed 2 to 3 components. The solvent was stripped from these fractions to give 254 mg. Preparatory thin layer chromatography of this material using silica gel plates (eluted with methylene chloride) afforded 150 mg of product comprising the title compound. m/e 701. PMR and CMR were consistent with the assigned structure.

The oxidative coupling of step (c) also was carried out as follows using aqueous potassium permanganate as the oxidant and tetra-n-butylammonium bromide as phase transfer catalyst:

A solution of 5.0 g (11.4 mmole) of the methyl ester compound prepared in step (b), 3.0158 g (11.4 mmole) of the compound prepared in step (a) and 184 mg (5% mole equivalent) of tetra-n-butylammonium bromide in 200 ml methylene chloride was cooled to 5° C. Then a solution of 1.8027 g (11.4 mmole) of potassium permanganate in 50 ml water was added dropwise over about 40 minutes. The mixture was allowed to stir in the cold for an hour, then allowed to warm to room temperature. The methylene chloride layer was filtered to remove $MnO_2$ and the filtrate washed with 100 ml 10% sodium bisulfite solution, one-half saturated sodium chloride solution and then dried over sodium sulfate. The sodium sulfate was filtered off, the solution concentrated to about 50 ml and chromatographed using high pressure liquid chromatography on a silica gel column. The column was eluted as follows: methylene chloride:-hexane (1:1) 2 liters; methylene chloride:hexane (2:1) 2 liters; methylene chloride:hexane (3:1) 5 liters; methylene chloride 2 liters. The fractions corresponding to the product were combined and the solvent evaporated to afford 2.9 g of the compound of Example 2. m/e 700

A sample of this compound was purified as follows: Approximately 1.6 g was taken up in about 14 ml hexanes with mild heating as necessary, then filtered through a filter syringe (0.45μm PTFE) and stored in the freezer for 4 days to afford large crystals. The solvent was decanted and the crystalline material dried in vacuo to afford 1.41 g of purified product.

The following experiment was conducted to confirm the conversion of this colorless precursor to the dye upon heating.

The compound of Example 2 (10 mg) was dissolved in 1.0 ml xylenes and heated under argon in an oil bath at 140°-150° C. An aliquot was removed at 10 minutes and diluted 1:20 with methanol. High pressure liquid chromatography of the aliquot showed that the yellow dye having the following structure and methyl p-hydroxybenzoate were formed cleanly, as demonstrated by coinjection with independently synthesized authentic samples.

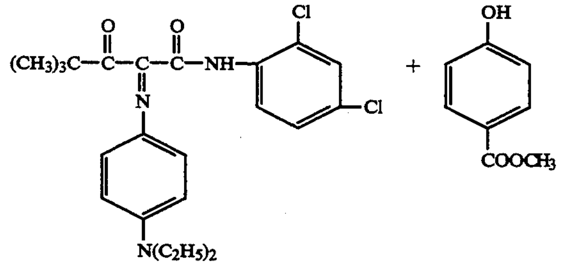

(The isobutylene and carbon dioxide by-products volatilized from the xylene solution during heating.)

EXAMPLES 3-8

Six compounds were prepared, Compounds 3 to 8 of the formula

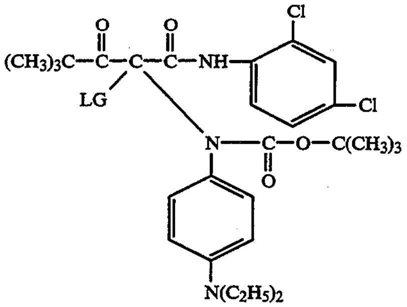

wherein the phenoxide group (LG) was varied as shown below. The procedure employed comprised the oxidative coupling of Example 2 using the oxidant specified and the coupler derivatized with the specified LG group.

| Compound | LG | Oxidant |
|---|---|---|
| 3 | 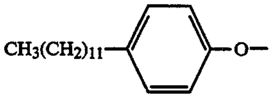 | $KMnO_4$ |
| 4 | 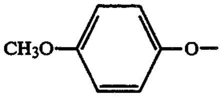 | $KMnO_4$ and $K_3Fe(CN)_6$ |
| 5 | 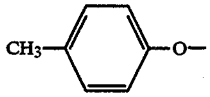 | $K_3Fe(CN)_6$ |
| 6 | 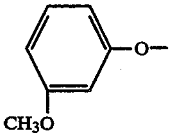 | $KMnO_4$ and $K_3Fe(CN)_6$ |
| 7 | 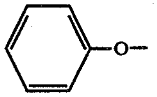 | $K_3Fe(CN)_6$ |
| 8 | 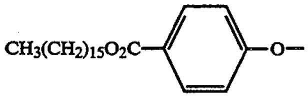 | $K_3Fe(CN)_6$ |

EXAMPLE 9

The compound of the formula

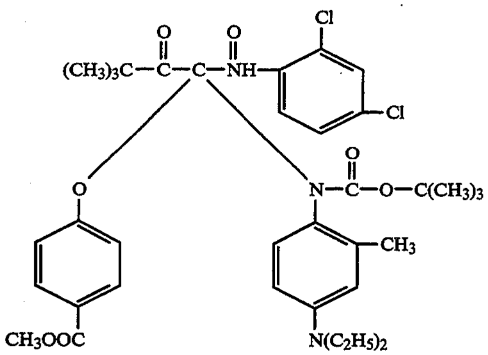

was prepared by oxidative coupling as in Example 2 using potassium permanganate as the oxidant and the phenylenediamine derivative possessing an ortho-methyl group having the formula

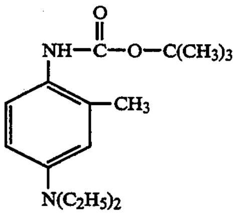

EXAMPLE 10

Preparation of the compound having the formula

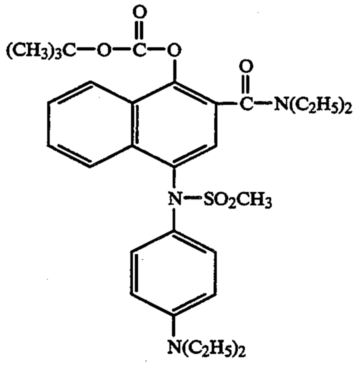

(a) To 50 ml of ethyl acetate was added 10 g (0.0041 mole) of the coupler of the formula

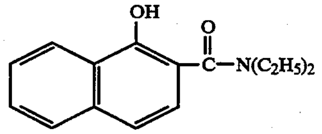

and 1.0 g (0. 0041 mole ) of the phenylenediamine derivative of the formula

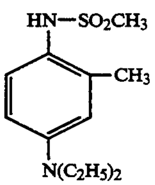

To this solution was added 4.0 g of potassium carbonate dissolved in 40 ml of water, followed by the dropwise addition of 2.2 g (0.0082 mole) of potassium ferricyanide in 20 ml water with vigorous agitation. After the addition was completed, the reaction mixture was stirred for several minutes. The ethyl acetate layer was collected, washed twice with brine, dried over sodium sulfate and evaporated to dryness. The residue was dissolved in a small amount of methylene chloride and chromatographed from 50:50 ethyl acetate/hexanes on a silica gel packed column. The following compound was collected.

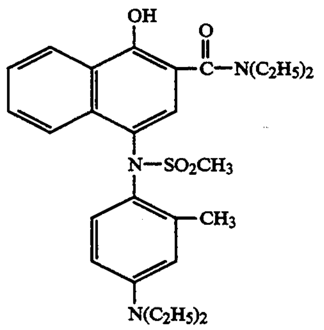

(b) 500 mg (1.0 mmole) of the compound prepared in step (a) was dissolved in 5 ml of methylene chloride with stirring. To this solution was added 125 mg (1.0 mmole) of 4-dimethylaminopyridine and 220 mg (1.0 mmole) of di-tert-butyl dicarbonate in 2 ml of methylene chloride. The resulting reaction mixture was stirred at room temperature for a few hours, and after the reaction appeared complete, the mixture was filtered through a plug of silica gel. The purified material was collected and evaporated to dryness. On standing for 48 hours, crystallization occurred and the desired material was triturated in hexanes and collected in a Buchner funnel to give approximately 180 mg of the title compound as a white solid. m/e 598; UV and IR spectra, and thermal gravimetric analysis were consistent with the assigned structure.

EXAMPLE 11

Preparation of the compound having the formula

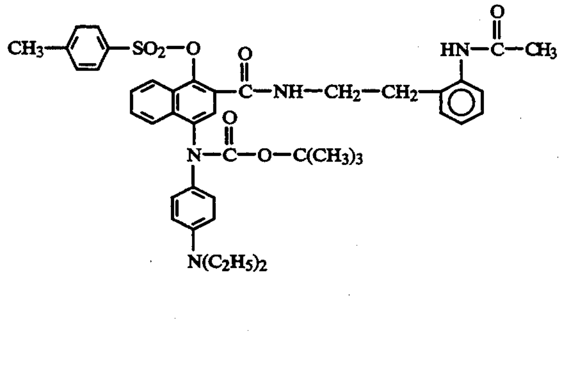

(a) 400 ml of 5% aqueous sodium carbonate solution was added to a slurry of 3.48 g (0.01 mol) of the coupler of the formula

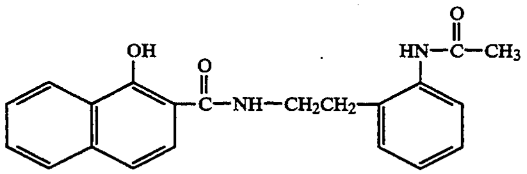

and 2.65 g ( 0.01 mol ) of the phenylenediamine derivative of the formula

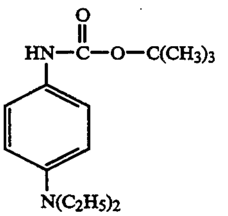

in 100 ml of ethyl acetate. Then a solution of 7 g (0.021 mol) of potassium ferricyanide in 100 ml water was added all at once to the above mixture. This was stirred vigorously for about one hour. The mixture was allowed to stand overnight and the crude reaction chromatographed using high pressure liquid chromatography on a silica gel column eluted with: methylene chloride, 2 liters; 1% methanol/methylene chloride, 2 liters; 2% methanol/methylene chloride, 2 liters. The solvent was evaporated from the fraction containing the desired product to give 3.48 g (57% yield by weight) of the compound having the formula

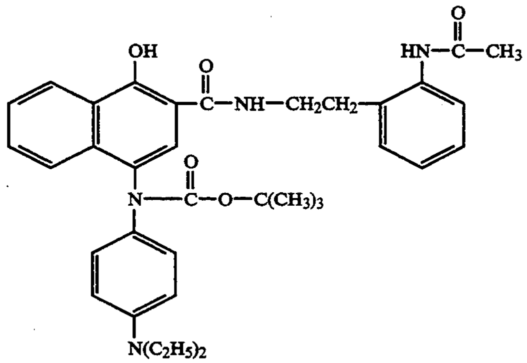

(b) A solution of 500 mg (0.82 mmol) of the compound prepared in step (a), and 0.115 ml (82.8 mg, 0.82 mmol) of triethylamine in 10 ml methylene chloride was cooled to about 5° C. Then a solution of 156.3 mg (0.82 mmol) of tosyl chloride dissolved in 5 ml methylene chloride was added dropwise to the above solution. The mixture was allowed to warm to room temperature. After stirring for 2 hours, the material was chromatographed using a gravity column (25 mm×210 mm) of silica gel which was eluted with 1.5% methanol/methylene chloride. Evaporation of the solvent afforded 595 mg (95% by weight yield) of the title compound. m/e 764. PMR and CMR were consistent with the assigned structure.

EXAMPLE 12

Preparation of the compound having the formula

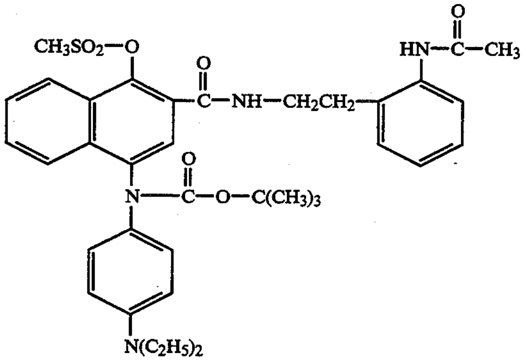

The title compound was prepared using the procedure given in Example 11 except that 99 mg (0.86 mmol of methanesulfonyl chloride was used in step (b). 520 mg (92 % yield by weight) of the title compound was obtained. m/e 690. PMR and CMR were consistent with the assigned structure.

The dyes obtained upon heating the colorless precursors of Examples 10 to 12 had the formulae

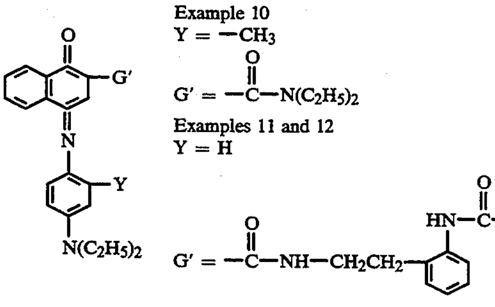

Besides the colorless precursor compounds of Examples 2 to 9 that form yellow azomethine dyes upon heating and of Examples 10 to 12 that form cyan indoaniline dyes upon heating, the following compounds are illustrative of colorless precursors of the present invention that undergo thermal activation to form magenta azomethine dyes.

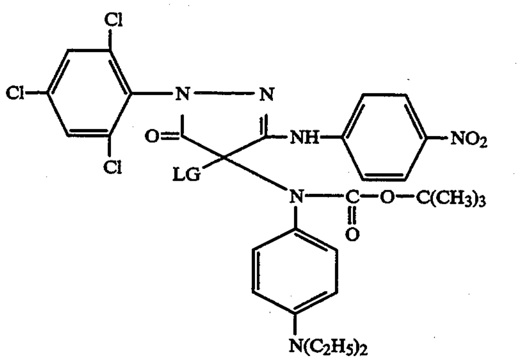
(13)

-continued

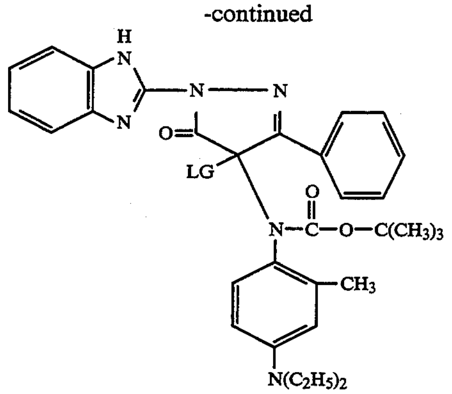
(14)

In producing images according to the present invention, the way in which the heat is applied or induced imagewise may be realized in a variety of ways, for example, by direct application of heat using a thermal printing head or thermal recording pen or by conduction from heated image-markings of an original using conventional thermographic copying techniques. Preferably, selective heating is produced in the image-forming layers by the conversion of electromagnetic radiation into heat and preferably, the light source is a laser beam emitting source such as a gas laser or semiconductor laser diode. The use of a laser beam is not only well suited for recording in a scanning mode but by utilizing a highly concentrated beam, photo-energy can be concentrated in a small area so that it is possible to record at high speed and high density. Also, it is a convenient way to record data as a heat pattern in response to transmitted signals such as digitized information and a convenient way of preparing multicolor images by employing a plurality of laser beam sources that emit laser beams of different wavelengths.

In the latter embodiment an infra-red absorbing substance is employed for converting infra-red radiation into heat which is transferred to the heat-sensitive colorless dye precursor compound to initiate the departure of the protecting group and the leaving group to form color images. Obviously, the infra-red absorber should be in heat-conductive relationship with the heat-sensitive compound, for example, in the same layer as the heat-sensitive compound or in an adjacent layer. Preferably, the infra-red absorber is an organic compound, such as, a cyanine, merocyanine or thiopyrylium dye and preferably, it is substantially non-absorbing in the visible region of the electromagnetic spectrum so that it will not add any substantial amount of color to the Dmin areas, i.e., the highlight areas of the image.

In the production of multicolor images, infra-red absorbers may be selected that absorb radiation at different wavelengths above 700 nm, which wavelengths usually are about 40 nm apart. Thus each imaging layer may be exposed independently of the others by using an appropriate infra-red absorber. As an illustration, the layers of heat-sensitive compound for forming yellow, magenta and cyan may have infra-red absorbers associated therewith that absorb radiation at 760 nm, 820 nm and 1100 nm, respectively, and may be addressed by laser beam sources, for example, infra-red laser diodes emitting laser beams at these respective wavelengths so that the yellow imaging layer can be exposed independently of the magenta and cyan imaging layers, the magenta imaging layer can be exposed independently of the yellow and cyan imaging layers, and the cyan imaging layer can be exposed independently of the yellow and magenta imaging layers. While each layer may be exposed. in a separate scan, it is usually preferred to expose all of the imaging layers simultaneously in a single scan using multiple laser beam sources of the appropriate wavelengths. Rather than using superimposed imaging layers, the heat-sensitive compounds and associated infra-red absorbers may be arranged in an array of side-by-side dots or stripes in a single recording layer.

In a further embodiment, multicolor images may be produced using the same infra-red absorbing compound in association with each of two or more superimposed imaging layers and exposing each imaging layer by controlling the depth of focussing of the laser beam. In this embodiment, the concentration of infra-red absorber is adjusted so that each of the infra-red absorbing layers absorb approximately the same amount of laser beam energy. For example, where there are three infra-red absorbing layers, each layer would absorb about one-third of the laser beam energy. It will be appreciated that controlling the focussing depth to address each layer separately may be carried out in combination with the previous embodiment of using infra-red absorbers that selectively absorb at different wavelengths in which instance the concentration of infra-red absorber would have to be adjusted for the laser beam energy since the first infra-red dye would not absorb any substantial amount of radiation at the absorption peaks of the second and third dyes and so forth.

Where imagewise heating is induced by converting light to heat as in the embodiments described above, the heat-sensitive element may be heated prior to, during or subsequent to imagewise heating. This may be achieved using a heating platen or heated drum or by employing an additional laser beam source for heating the element while it is being exposed imagewise.

The heat-sensitive elements of the present invention comprise a support carrying at least one imaging layer of the above denoted heat-sensitive compounds and may contain additional layers, for example, a subbing layer to improve adhesion to the support, interlayers for thermally isolating the imaging layers from each other, infra-red absorbing layers as discussed above, anti-static layers, an anti-abrasive topcoat layer which also may function as a UV protecting layer by including an ultraviolet absorber therein or other auxiliary layers. For example, an electroconductive layer may be included and imagewise color formation effected by heat energy generated in response to an electrical signal.

The heat-sensitive compounds are selected to give the desired color or combination of colors, and for multicolor images, the compounds selected may comprise the additive primary colors red, green and blue, the subtractive primaries yellow, magenta and cyan or other combinations of colors, which combinations may additionally include black. As noted previously, the compounds generally are selected to give the subtractive colors cyan, magenta and yellow commonly employed in photographic processes to provide full natural color. Also, a compound that forms a black dye can be selected for providing a black image.

The support employed may be transparent or opaque and may be any material that retains its dimensional stability at the temperature used for image formation. Suitable supports include paper, paper coated with a resin or pigment, such as, calcium carbonate or calcined clay, synthetic papers or plastic films, such as polyethylene, polypropylene, polycarbonate, cellulose acetate, polyethylene terephthalate and polystyrene.

Usually the layer of heat-sensitive compound contains a binder and is formed by combining the heat-sensitive compound and a binder in a common solvent, applying a layer of the coating composition to the support, and then drying. Rather than a solution coating, the layer may be applied as a dispersion or an emulsion. The coating composition also may contain dispersing agents, plasticizers, defoaming agents, coating aids and materials such as waxes to prevent sticking where thermal recording heads or thermal pens are used to apply the imagewise pattern of heat. In forming the layer(s) containing the heat-sensitive compounds and the interlayers or other layers, temperatures should be maintained below levels that will initiate the fragmentation reaction so that the heat-sensitive compounds will not be prematurely colored.

Any of the binders commonly employed in heat-sensitive recording elements may be employed provided that the binder selected is inert, i.e., does not have any adverse effect on the heat-sensitive compound incorporated therein. Also, the binder should be heatstable at the temperatures encountered during image formation and it should be transparent so that it does not interfere with viewing of the color image. Where electromagnetic radiation is employed to induce imagewise heating, the binder also should transmit the light intended to initiate image formation. Examples of binders that may be used include polyvinyl alcohol, polyvinyl pyrrolidone, methyl cellulose, cellulose acetate butyrate, copolymers of styrene and butadiene, polymethyl methacrylate, copolymers of methyl and ethyl acrylate, polyvinyl acetate, polyvinyl chloride, poly(ethyloxazoline), polyvinyl butyral and polycarbonate.

As an illustration of the thermal "coloration" of the compounds of the present invention, the compounds of Examples 1 and 2 were coated on a white pigmented polyester support by combining the compound (10 mg) with 0.5 ml of 2% by weight poly(ethyloxazoline) in methylene chloride, applying a layer of the coating composition to the support using a #16 Meyer Rod and then drying the coating. The compound of Example 12 was coated on a white pigmented polyester support in the same manner except that 15 mg of compound was combined with 0.5 ml of 2% by weight poly(ethyloxazoline) in tetrahydrofuran. The compound of Example 10 was coated on a white pigmented polyester support in the same manner as Example 12 except that 20 mg of compound was combined with 1 ml of 2% by weight poly(ethyloxazoline) in tetrahydrofuran. The coating composition also contained 0.06% by weight of an infrared absorber having the structural formula set out below designated IR Compound. After air-drying, an overcoat layer of a butadiene-styrene copolymer latex was applied using a #14 Meyer Rod and air dried.

A strip of the coated material containing the compound of Example 1 was placed on a hot plate preheated to 190° C. and yellow color formation was measured after 3 minutes. The maximum reflection density obtained was 0.93. The reflection density measured before heating was 0.59.

A strip of the coated material containing the compound of Example 2 was placed on a hot plate preheated to 191° C. and yellow color formation was measured at different time intervals. The maximum reflection density measured after 30 seconds was 0.96 and after 60 seconds was 0.82. The reflection density measured before heating was 0.12.

A strip of the coated material containing the compound of Example 12 was placed on a hot plate preheated to 190° C. and cyan color formation was measured after 2 minutes. The maximum reflection density obtained was 0.72. The reflection density before heating was 0.09.

A strip of the coated material containing the Compound of Example 10 was placed on a hot plate preheated to 191° C., and the maximum reflection density obtained after two minutes was 1.31. The reflection density before heating was 0.09.

The reflection densities were measured using an X-Rite Model 338 reflection densitometer equipped with the appropriate filter.

In a further experiment, the compounds of Examples 2 to 9 and 11 were combined with a solution of 2% by weight polymer binder in a solvent containing an infra-red absorber. The quantity of each compound added to the polymer solution in terms of g/ml and the concentration of infra-red absorber in terms of % by weight are given in the following Table wherein Solution A represents 2% by weight polycarbonate in tetrahydrofuran, Solution B represents 2% by weight polycarbonate in methylene chloride, Solution C represents 2% by weight poly(ethyloxazoline) in tetrahydrofuran and Solution D represents 2% by weight poly(ethyloxazoline) in methylene chloride. The structural formula for the infra-red absorber employed is set out below.

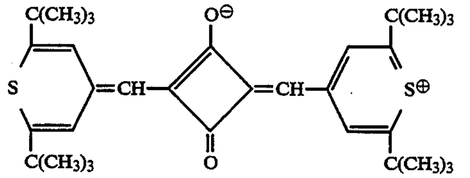

IR Compound

The coating compositions thus prepared were applied to a white pigmented polyester support using a #16 Meyer Rod. After air drying overnight, an overcoat layer of butadiene-styrene copolymer latex was applied using a #14 Meyer Rod and the overcoated samples again were air dried overnight.

The coated samples were irradiated at five different scanning rates using a laser diode emitting at a wavelength of 825 nm and at an output of 200 m Watts which was approximately 120 m Watts at the film plane. The scanning rates employed were 0.5; 0.75; 1.0; 1.25 and 1.5 microns per microsecond, respectively, for each sample. The maximum reflection density (Dmax) measured for each scan and the initial density of each coating (Dmin) are set forth in the Table.

TABLE

| Compound (Example) | Polymer Solution | Amount (g/ml) | IR Dye (wt. %) | Dmax (μ/μ sec) (0.50-0.75-1.00-1.25-1.50) | Dmin |
|---|---|---|---|---|---|
| 2 | A | 0.0200 | 0.06 | 1.57 1.52 1.48 1.33 1.09 | 0.09 |
| 3 | B | 0.0231 | 0.07 | 1.36 1.31 1.07 0.75 0.59 | 0.10 |
| 4 | B | 0.0191 | 0.07 | 1.34 1.31 1.38 1.26 1.15 | 0.10 |
| 5 | A | 0.0187 | 0.06 | 1.30 0.83 0.67 0.59 0.47 | 0.09 |
| 6 | C | 0.0192 | 0.06 | 1.30 1.15 0.97 0.75 0.59 | 0.12 |
| 7 | A | 0.0183 | 0.06 | 1.74 1.34 1.11 0.78 0.55 | 0.09 |
| 8 | A | 0.0260 | 0.06 | 1.26 1.13 0.95 0.72 0.53 | 0.12 |
| 9 | A | 0.0204 | 0.06 | 1.85 1.52 1.23 1.01 0.77 | 0.14 |
| 11 | D | 0.0167 | 0.06 | 0.50 0.46 0.41 0.34 0.26 | 0.10 |

From the results presented above, it can be seen that color is formed at the various scanning rates in the heated areas of the sample coatings comprising the colorless precursor compounds with the compounds of Examples 2 to 9 forming yellow and the compound of Example 11 forming cyan.

It will be appreciated that the heat-sensitive compounds of the present invention and the heat-sensitive elements prepared therefrom may be used in various thermal recording systems including thermal printing, thermographic copying and, particularly, high-speed laser recording to provide high contrast, high resolution images suitable for viewable color prints and transparencies, color images requiring magnification such as microfilm, color filters for color displays and color sensors, optical disks and so forth. Depending upon the particular application, the heat-sensitive elements may contain thermal isolating layers, reflective, subcoat, topcoat or other layers, and the various layers including the imaging layer(s) together with any infra-red absorbing layer(s) may be arranged in the configuration as desired and appropriate.

Since certain changes may be made in the herein described subject matter without departing from the scope of the invention herein involved, it is intended that all matter contained in the above description and examples be interpreted as illustrated and not in a limiting sense.

We claim:

1. A colorless precursor of a preformed image dye substituted with (a) at least one thermally removable protecting group that undergoes fragmentation from said precursor upon heating and (b) at least one leaving group that is irreversibly eliminated from said precursor upon heating, provided that neither said protecting group nor said leaving group is hydrogen, said protecting and leaving groups maintaining said precursor in its colorless form until heat is applied to effect removal of said protecting and leaving groups whereby said colorless precursor is converted to an image dye.

2. A colorless precursor of a preformed image dye substituted with (a) at least one thermally removable protecting group that undergoes fragmentation from said precursor upon heating, said protecting group being selected from the group consisting of

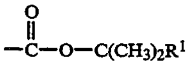

wherein $R^1$ is alkyl, halomethyl, or aryl, substituted or unsubstituted;

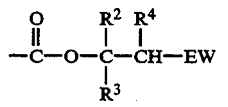

wherein $R^2$ and $R^3$ each are hydrogen, alkyl or aryl, $R^4$ is hydrogen, alkyl, aryl or EW and EW represents an electron-withdrawing group;

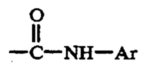

wherein Ar is aryl, substituted or unsubstituted;

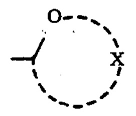

wherein X represents the atoms to complete 2-tetrahydropyranyl; and

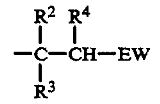

wherein $R^2$, $R^3$, $R^4$ and EW have the same meaning given above, and (b) at least one leaving group that is irreversibly eliminated from said precursor upon heating, provided that neither said protecting group nor said leaving group is hydrogen, said protecting and leaving groups maintaining said precursor in its colorless form until heat is applied to effect removal of said protecting and leaving groups whereby said colorless precursor is converted to an image dye.

3. The precursor as defined in claim 2 possessing a colorless chromophore bonded to at least one auxochrome and (1) one of said (a) protecting group(s) and said (b) leaving group(s) being bonded to an atom of said colorless chromophore and the other being bonded to said auxochrome or (2) both said (a) and (b) groups being bonded to different atoms of said colorless chromophore.

4. The precursor as defined in claim 3 which upon heating yields an image dye selected from the group consisting of an azomethine, indoaniline, indophenol, indamine, azine or di- and triarylmethane dye.

5. The precursor as defined in claim 2 which has the formula

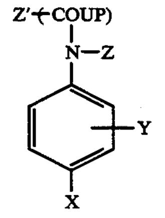

wherein:

COUP represents a dye-forming coupler moiety substituted in its coupling position with the remainder of the structure;

X is —NR'R" wherein R' and R" each are selected from hydrogen and alkyl containing 1 to 6 carbon atoms;

Y is hydrogen, alkyl, or substituted alkyl; and

Z and Z' each are selected from a thermally removable protecting group and a leaving group provided one of Z and Z' is said protecting group and the other is said leaving group.

6. The precursor as defined in claim 5 wherein said R' and R" each are ethyl.

7. The precursor as defined in claim 6 wherein Y is hydrogen.

8. The precursor as defined in claim 7 wherein Y is alkyl and is positioned ortho to said N-Z.

9. The precursor as defined in claim 8 wherein said dye-forming coupler moiety is selected from an acylacetanilide, a pyrazolone and a 1-hydroxy-2-naphthamide coupler moiety.

10. The precursor as defined in claim 2 wherein said protecting group, when positioned on nitrogen, is t-butoxycarbonyl.

11. The precursor as defined in claim 2 wherein said leaving group is represented by

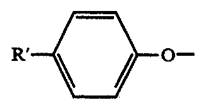

wherein R' is hydrogen, alkyl, or carboalkoxy.

12. The precursor as defined in claim 2 wherein said protecting group, when positioned on nitrogen, is t-butoxycarbonyl, and wherein said leaving group is represented by

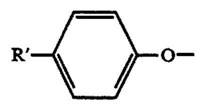

wherein R' is hydrogen, alkyl, or carbonalkoxy.

13. A colorless precursor of a preformed image dye which has the formula

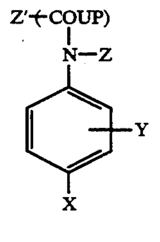

wherein

COUP is represented by

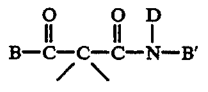

wherein B is selected from $(CH_3)_3C—$, $CH_3OCH_2(CH_3)_2C—$, $C_6H_5O(CH_3)_2C—$ and phenyl, unsubstituted or substituted with one or more groups selected from alkyl, alkoxy, nitro, halo, and carbonamido; B' is phenyl, unsubstituted or substituted with one or more groups selected from alkyl, alkoxy, nitro, halo, and carbonamido, said phenyl group B' being the same or different from said phenyl group B; D is hydrogen, alkyl, or acyl; Z is t-butoxycarbonyl; Y is hydrogen; X is —NR'R" wherein R' and R" each are selected from hydrogen and alkyl; and, Z' is represented by

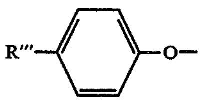

or

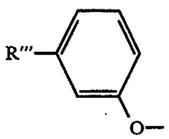

wherein R''' is hydrogen, alkyl or carboalkoxy.

14.

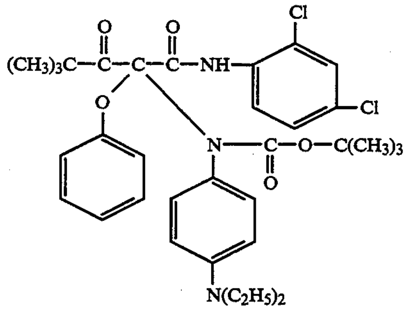

* * * * *